United States Patent [19]

Komatsu

[11] Patent Number: 5,006,070
[45] Date of Patent: Apr. 9, 1991

[54] DENTAL IMPLANT WITH Y-SHAPED BODY

[76] Inventor: Shigeru Komatsu, 7-14-7, Roppongi, Minato-ku, Tokyo, Japan

[21] Appl. No.: 404,113

[22] Filed: Sep. 7, 1989

[30] Foreign Application Priority Data

Feb. 27, 1989 [JP] Japan .................. 1-21915[U]

[51] Int. Cl.⁵ .................................................. A61C 8/00
[52] U.S. Cl. .................................. 433/176; 433/173
[58] Field of Search ............... 433/173, 174, 175, 176, 433/201.1

[56] References Cited

U.S. PATENT DOCUMENTS

| | | | |
|---|---|---|---|
| 2,449,522 | 9/1948 | White | 433/173 |
| 3,729,825 | 5/1973 | Linkow et al. | 433/176 |
| 3,798,771 | 3/1974 | Edelman | 433/176 |
| 3,977,081 | 8/1976 | Zambelli et al. | 433/176 |
| 3,979,828 | 9/1976 | Taylor | 433/201.1 |
| 4,180,910 | 1/1980 | Straumann et al. | 433/173 |
| 4,521,192 | 6/1985 | Linkow | 433/173 |
| 4,624,673 | 11/1986 | Meyer | 433/173 |
| 4,631,031 | 12/1986 | Richter | 433/173 |
| 4,722,688 | 2/1988 | Lonca | 433/201.1 |
| 4,768,956 | 9/1988 | Kurpis | 433/173 |
| 4,802,847 | 2/1989 | Komatsu | 433/176 |

FOREIGN PATENT DOCUMENTS

| | | | |
|---|---|---|---|
| 1148388 | 6/1983 | Canada | 433/173 |
| 2610819 | 8/1988 | France | 433/173 |

Primary Examiner—Gene Mancene
Assistant Examiner—Michael Lynch
Attorney, Agent, or Firm—Pretty, Schroeder, Brueggemann & Clark

[57] ABSTRACT

A dental implant comprises a Y-shaped body including three planar legs which have respective openings defined centrally in sides thereof and extend radially as viewed from above, and a head supported on the body and adapted to be capped by an artificial tooth. The three legs which extend radially outwardly allow the body to be firmly anchored in an alveolar bone of the patient. After the body has been embedded in a groove defined in the alveolar bone, the alveolar bone grows and is joined together through the openings in the legs. As a result, the embedded body becomes more and more secure with time.

12 Claims, 5 Drawing Sheets

DENTAL IMPLANT WITH Y-SHAPED BODY

BACKGROUND OF THE INVENTION

1. Field of the Invention

The present invention relates to a dental implant for mounting an artificial tooth on an alveolar bone, and more particularly to an improvement in the body of such a dental implant.

2. Description of the Relevant Art

Dental implants are available in various types and forms. One of such various implant types is known as a blade type implant having a blade-like body and was invented by L. I. Linkow. The other dental implant types, which followed the blade type implant, include a rod-shaped core bent type implant, an I.T.I. hollow cylinder type implant, and a wavy type implant. One wavy type dental implant is disclosed in U.S. Pat. No. 4,802,847 filed by the applicant of the present application. These prior dental implants have different configurations. Basically, however, each of the known dental implants comprises a body and a head supported on the body. After the body is embedded and fixedly mounted in a groove defined in an alveolar bone, an artificial tooth is capped over the head.

With the blade type dental implant, the head is supported on the body in the form of a planar blade. In order to make the implant strong and secure when the body is embedded in an alveolar bone, the blade must have a considerable length. Therefore, a relatively long groove for receiving the blade must be defined in the alveolar bone. As a result, a relatively time-consuming and complex operation is required on the user even when mounting a single artificial tooth.

When a rod-shaped core bent type dental implant or an I.T.I. hollow cylinder type dental implant is used, its body can be embedded in an alveolar bone without forming a considerably large groove in the bone. However, the body cannot sufficiently be fixed in place during an initial phase of the embedding process. Since any opening defined in the body is small, the alveolar bone which grows after the body has been embedded cannot securely be joined together through the opening in the body, and hence the body is not anchored firmly in place. Consequently, an artificial tooth mounted on the head is not sufficiently resistant to lateral pressures produced when upper and lower teeth of the user are pressed against each other. The artificial tooth is therefore apt to fail to withstand use over a long period of time.

According to the conventional dental implants, as described above, the structures of the bodies cause various disadvantages especially when only one artificial tooth is mounted.

SUMMARY OF THE INVENTION

According to the present invention, a dental implant comprises a body including three planar legs which have respective openings defined centrally in sides thereof and extend radially as viewed from above, and a head supported on the body and adapted to be capped by an artificial tooth. The dental implant is referred to as a Y type dental implant as the body is Y-shaped as viewed from above.

Since the three legs extend radially outwardly, the body can firmly be anchored in an alveolar bone of the user during an initial phase of the process by which the body is embedded in the bone in the operation. The dental implant thus constructed and mounted in the alveolar bone is strongly resistant to lateral pressures which are developed when upper and lower teeth of the user are pressed against each other after the operation. After the body has been embedded in a groove defined in the alveolar bone, the alveolar bone grows and is joined together through the openings in the legs. As a result, the embedded body becomes more and more secure with time.

The above and further details and advantages of the present invention will become apparent from the following detailed description of preferred embodiments thereof, when read in conjunction with the accompanying drawings.

DETAILED DESCRIPTION OF THE PREFERRED EMBODIMENTS

A dental implant according to a first embodiment of the present invention will be described with reference to FIGS. 1 through 5.

A Y-type dental implant 1 is of a unitary structure made of pure titanium which is of high affinity with living organisms and is highly resistant to corrosion. The Y-type dental implant 1 comprises a body 3 and a head 5 supported on the body 3 and adapted to be capped by an artificial tooth.

Figure 1:
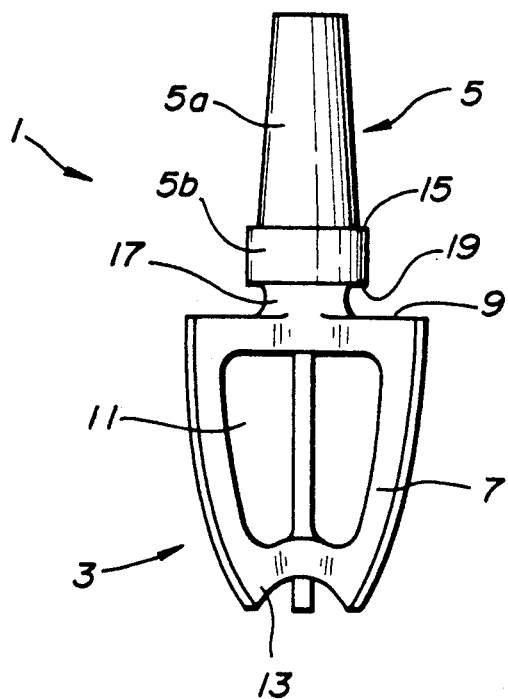
FIG. 1 is a front elevational view of a Y type dental implant according to a first embodiment of the present invention.
Figure 2:
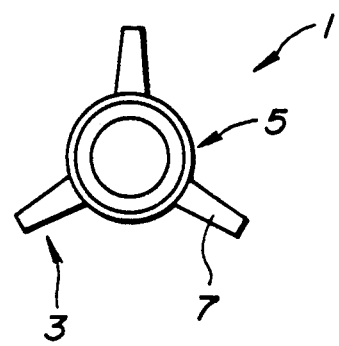
FIG. 2 is a plan view of the Y type dental implant
Figure 3:
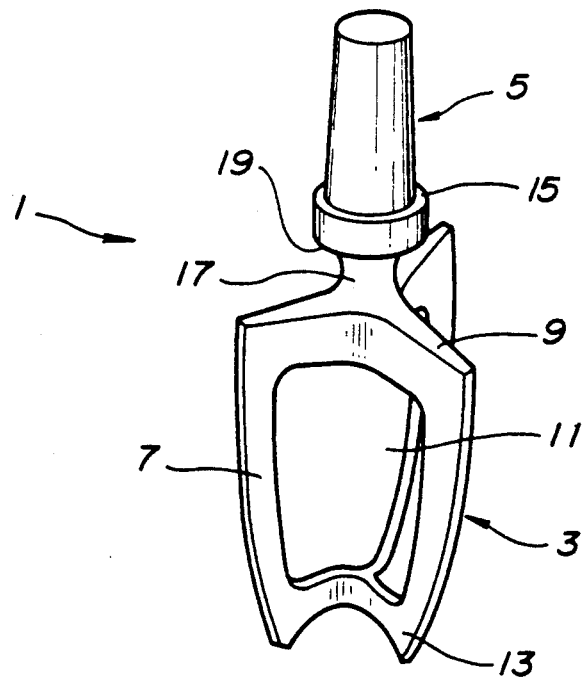
FIG. 3 is a perspective view of the Y type dental implant.

The body 3 comprises three legs 7 which are vertically long, have a substantially uniform thickness, and a substantially identical shape. As shown in FIG. 2, the legs 7 extend radially outwardly and are spaced at substantially equal angular intervals as viewed from above. Therefore, the legs 7 are angularly spaced at 120° in the illustrated embodiment. However, the angles between the legs 7 may be varied depending on the configuration of an alveolar bone of the user or patient in which the dental implant 1 will be embedded. The radial arrangement of the legs 7 allows the body 3 to be firmly anchored in the alveolar bone during an initial phase of the embedding process. The radial legs 7 are also highly resistant to lateral pressures which will be exerted to the artificial tooth when upper and lower teeth of the user are pressed against each other after the operation.

The legs 7 have substantially flat shoulders 9 respectively on their upper ends. Each of the legs 7 has an opening 11 defined centrally in its side and occupying a substantial portion of the leg 7. Therefore, each leg 7 is in the form of a peripheral frame. The legs 7 are joined to each other at their upper and lower ends at the central portion of the body 3. The openings 11 in the respective legs 7 communicate with each other or are joined to each other at the central portion of the body 3.

After the body 3 has been embedded in the alveolar bone, the openings 11 allow a blood stream to flow freely therethrough, so that the alveolar bone will grow well into the openings 11 and be joined together. Accordingly, the body 3 in the alveolar bone becomes more and more secure with time. The openings 11 may not communicate with each other, but may be defined independently in the respective legs 7. With such a modification, the legs 7 are joined to each other all the way along the center of the body 3, and the openings 11 are defined independently in the respective sides of the legs 7.

The legs 7 have on their outer lower ends respective feet 13 extending downwardly and having pointed tips, which permit the body 3 to enter easily into the alveolar bone when the body 3 is pressed into the bone. The feet may be provided on the inner lower ends of the legs 7 at the center of the body 3, so that their pointed tips are positioned at the center of the body 3.

The head 5 is of a frustoconical shape and has an upper smaller-diameter portion 5a and a lower larger-diameter portion 5b which is larger in diameter than the upper portion 5a, with a positioning step 15 defined between the upper and lower portions 5a, 5b. When an artificial tooth is capped over the head 5, the positioning step 15 abuts against the bottom of the crown of the artificial tooth and holds the crown. The head 5 is supported on the body 3 by means of a smaller-diameter neck 17 on the upper central end of the body 3, the neck 17 being smaller in diameter than the larger-diameter portion 5b. A step at the boundary between the larger-diameter portion 5b and the neck 17 serves as a safety stop 19 for holding the body 3 within the dense bone in the upper layer of the alveolar bone, so that the body 3 will not sink into the relatively soft cancellous bone in the lower layer of the alveolar bone. When the dental implant 1 is embedded in alveolar bone, the larger-diameter portion 5b of the head 5 remains exposed above the bone.

Figure 4:
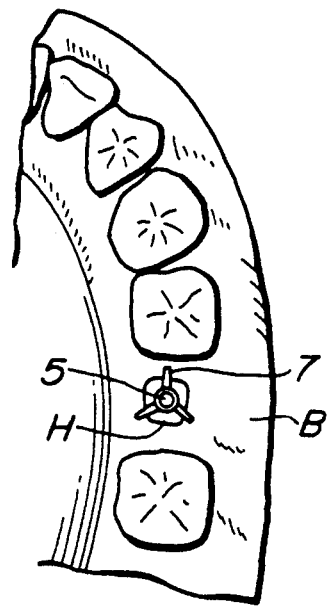
FIG. 4 is a fragmentary plan view showing the dental implant of FIG. 1 which is embedded in an alveolar bone.
Figure 5:
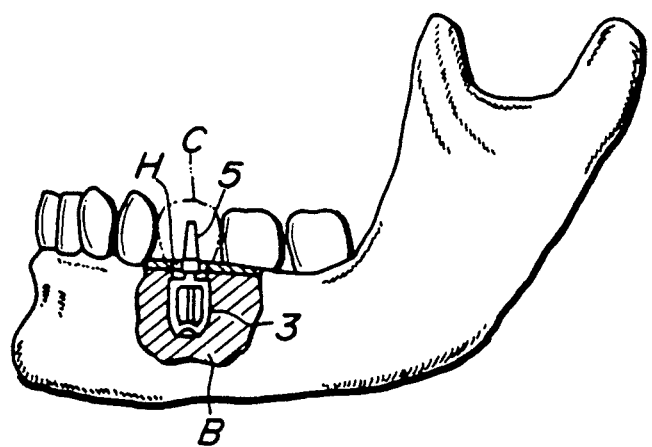
FIG. 5 is a front elevational view, partly cut away, of the dental implant as embedded in the bone.

As described above, since the dental implant 1 of the present invention is firmly anchored in position, a single artificial tooth can be mounted on the dental implant 1. As shown in FIGS. 4 and 5, even right after a tooth has been pulled out, a cavity H left in an alveolar bone B from which the tooth has been pulled out can be used to receive the body 3 provided the cavity H is slightly shaped by a dental cutting tool.

By pressing the body 3 into the cavity H, the pointed feet 13 on the lower ends of the legs which extend radially outwardly in three directions are easily forced into the alveolar bone B, so that the dental implant 1 can be mounted on the bone B. At this time, the portion of the dental implant 1 up to the upper end of the neck 17 is embedded in the alveolar bone B, and the larger-diameter portion 5b of the head 5 remains outside of the bone B. The larger-diameter portion 5b will be covered with the gum upon growth thereof after the operation. Therefore, only the smaller-diameter portion 5a of the head 5 will remain exposed out of the gum, and the crown C of an artificial tooth is capped over the exposed smaller-diameter portion 5a. Since the body 3 is vertically long as with a natural tooth, it can neatly be implanted between two adjacent existing teeth with utmost ease.

A dental implant according to a second embodiment of the present invention will be described below with reference to FIGS. 6 through 9. Those parts shown in FIGS. 6 through 9 which are identical to those of FIGS. 1 through 5 are denoted by identical reference numerals, and will not be described in detail.

Figure 6:
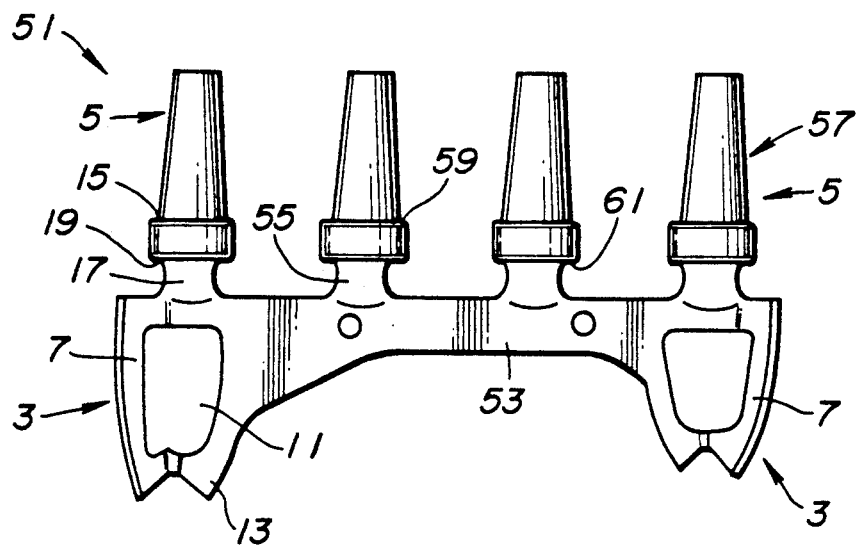
FIG. 6 is a front elevational view of a dental implant according to a second embodiment.
Figure 8:
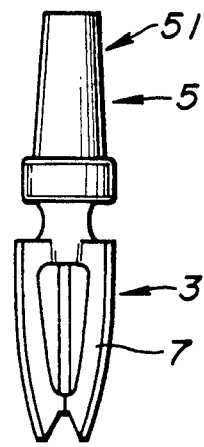
FIG. 8 is a side elevational view of the dental implant shown in FIG. 6.

As shown in FIG. 6, a dental implant 51 according to the second embodiment includes two dental implants 1 (FIG. 1) interconnected laterally by means of a joint member 53. One of the legs 7 of one of the bodies 3 is integrally joined to one of the legs 7 of the other body at upper outer edges of these legs 7 by the joint member 53 which is of substantially the same thickness as that of the legs 7.

Two heads 7 which are identical to the head 5 (FIG. 1) are supported at equally spaced intervals on the upper edge of the joint member 53 through respective necks 55. The heads 57 have respective steps 59 on their lower outer peripheries for holding the crowns of artificial teeth to prevent them from sinking into an alveolar bone, and safety stops 61 on the lower ends of the heads 57 for preventing the joint member 53 from sinking into the alveolar bone.

Figure 7:
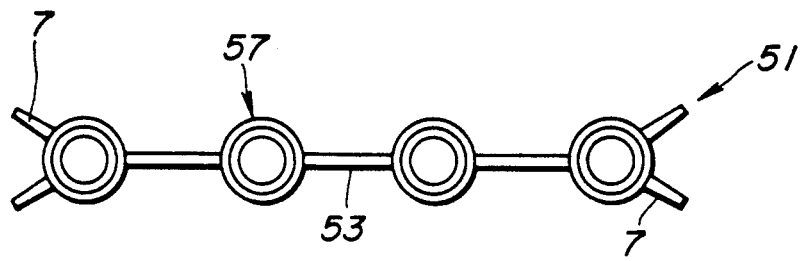
FIG. 7 is a plan view of the dental implant shown in FIG. 6.
Figure 9:
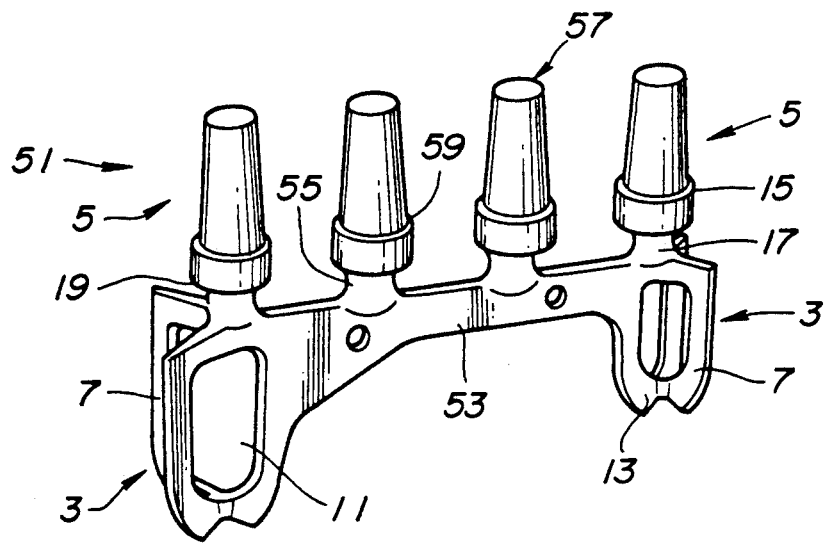
FIG. 9 is a perspective view of the dental implant shown in FIG. 6.

The dental implant 51 may be structurally modified in various ways. For example, as shown in FIG. 7, the angle between two adjacent legs 7 of each of the bodies 3, which angle is remote from the joint member 53, may be smaller than the other angles between the legs 7. As shown in FIG. 6, the bodies 3 on the opposite ends of the joint member 53 may be of different sizes. Further, the number of heads 57 may be varied. Thus, the design of the dental implant 51 may be modified depending on the area on an alveolar bone where it is to be embedded, and the number of teeth to be replaced with artificial teeth.

Figure 10:
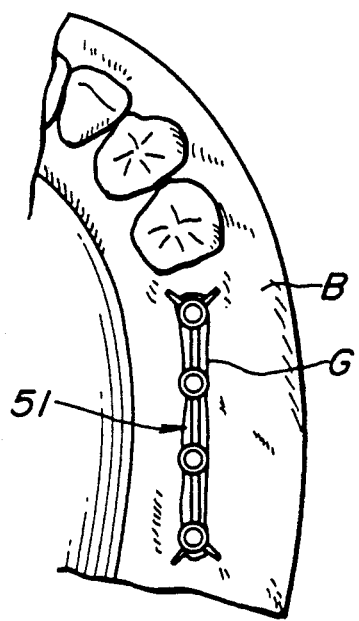
FIG. 10 is a fragmentary plan view showing the dental implant of FIG. 6 which is embedded in an alveolar bone.
Figure 11:
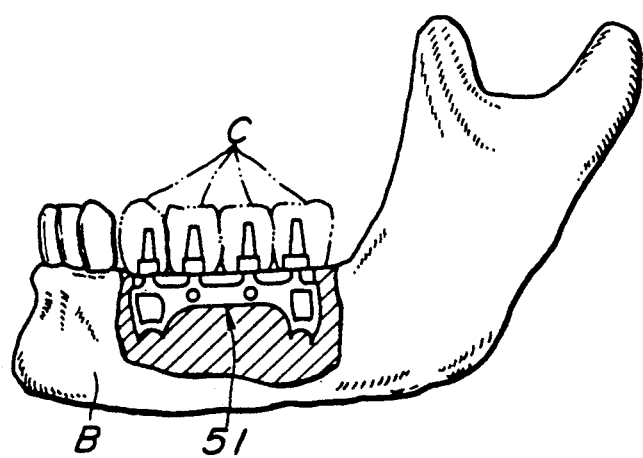
FIG. 11 is a front elevational view, partly cut away, of the dental implant of FIG. 6 as embedded in the bone.

The manner in which the dental implant 51 is used will be described below with reference to FIGS. 10 and 11. In order to anchor the dental implant 51 to an alveolar bone B, a groove G having a width, ranging from 1.2 to 1.8 mm, which is slightly smaller than the diameter of the body 3, and a length which is slightly larger than the entire length of the implant 51, is defined in the alveolar bone B where artificial teeth are to be mounted. Then, the bodies 3 are pressed into the groove G. The dental implant 51 will then be embedded in the same manner as the dental implant 1. The dental implant 51 can easily be embedded as it requires no special tool.

According to the second embodiment, the dental implant 51 can install a number of artificial teeth. As with the dental implant 1 which installs a single artificial tooth, the dental implant 51 is firmly anchored in position during an initial phase of the embedding process, and remains securely mounted on the alveolar bone over a long period of time since the implant 51 is highly resistant to lateral pressures applied thereto.

In each of the first and second embodiments, the head 5 or each of the heads 5 may be detachably supported on the body 3.

Figure 12:
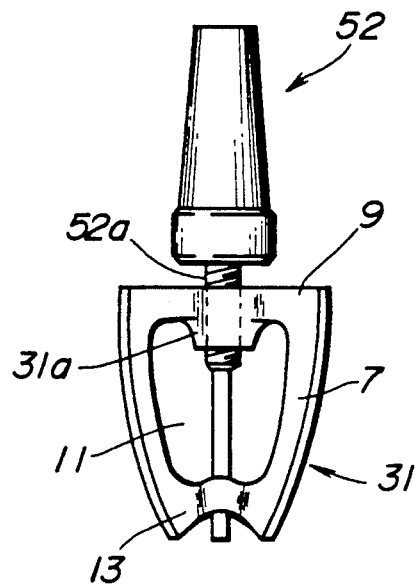
FIG. 12 is a front elevational view of a modification of the dental implant of FIG. 1, with a detachable head.
Figure 13:
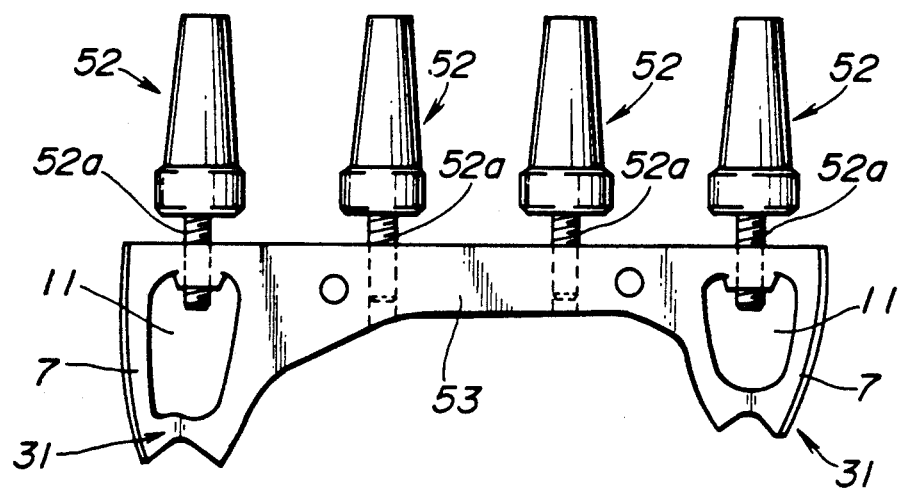
FIG. 13 is a front elevational view of a modification of the dental implant of FIG. 6, with detachable heads.

More specifically, as shown in FIG. 12, a head 52 is separate from a body 31 and has an externally threaded rod 52a extending from the lower end thereof. The body 31 has an internally threaded boss 31a in an upper central portion thereof for threaded engagement with the externally threaded rod 52a. The head 51 is detachably supported on the body 3 by threading the externally threaded rod 52a into the internally threaded boss 31a of the body 3. After the body 31 has been embedded in an alveolar bone, the alveolar bone grows and is joined together through the openings 11 in three to six months until the body 31 is firmly anchored in the alveolar bone. Then, the head 51 is attached to the body 31. According to another modification shown in FIG. 13, heads 52 are detachably supported on the bodies 3 and the joint member 53 through the threaded engagement as shown in FIG. 12.

With the present invention, as described above, the Y type dental implant is firmly anchored during an initial phase of the embedding process when at least one artificial tooth is to be mounted. Since the Y type dental implant is highly resistant to lateral pressures, it remains securely held in position over a long period of time. The alveolar bone in which the cavity for receiving the implant is formed will grow well after the operation because a blood flow is not prevented by the body embedded in the alveolar bone. The dental implant can easily be embedded without the need for any special tool. A plurality of dental implant bodies may be interconnected to mount a plurality of artificial teeth.

Although there have been described what are at present considered to be the preferred embodiments of the present invention, it will be understood that the invention may be embodied in other specific forms without departing from the essential characteristics thereof. The present embodiments are therefore to be considered in all aspects as illustrative, and not restrictive. The scope of the invention is indicated by the appended claims rather than by the foregoing description.

I claim:

1. A dental implant comprising:
 a body including three planar legs extending radially as viewed from above, each of said legs having an opening defined centrally therein with said centrally defined openings being in communication with each other such that the legs define a peripheral frame about a central cavity; and wherein each of said legs has a tapered foot that extends downwardly and terminates in a downwardly pointed tip at a lower end remote from a head; and
 the head supported on said body and adapted to be capped by an artificial tooth.

2. A dental implant according to claim 1, wherein said legs are angularly spaced at equal angular intervals.

3. A dental implant according to claim 1, wherein said head is of a frustoconical shape.

4. A dental implant according to claim 1, wherein said head has an upper smaller-diameter portion, a lower larger-diameter portion which is larger in diameter than said upper smaller-diameter portion, and a positioning step disposed between said upper smaller-diameter portion and said lower larger-diameter portion, said positioning step being adapted to abut against the bottom of the artificial tooth when said head is capped by the artificial tooth.

5. A dental implant according to claim 4, wherein said head is supported on an upper central end of said body by means of a neck which is smaller in diameter than said lower larger-diameter portion of said head.

6. A dental implant according to claim 1, wherein said head and said body are separate from each other, said head having an externally threaded rod joined to a lower end thereof, said body having an internally threaded boss in an upper central portion thereof, said head being detachably supported on said body with said externally threaded rod being threaded in said internally threaded boss.

7. A dental implant according to claim 1, wherein said body and said head are made of pure titanium.

8. A dental implant according to claim 1, wherein said body and said head are formed integrally as a unit.

9. A dental implant according to claim 1, wherein said head has a safety stop formed on the lower end thereof for holding said body within the dense bone of the alveolar bone when said implant is in position.

10. A dental implant comprising:
 a pair of bodies each including three planar legs having respective openings defined centrally in sides thereof and extending radially as viewed from above; said centrally defined openings being in communication with each other such that the legs define a peripheral frame about a central cavity; wherein each of said legs has a tapered foot that extends downwardly and terminates in a downwardly pointed tip at a lower end remote from a head;
 the head supported on each of said bodies and adapted to be capped by an artificial tooth; and
 a joint member interconnecting one of said legs of one of said bodies and one of said legs of the other body.

11. A dental implant according to claim 10, further including at least one head supported on an upper edge of said joint member and adapted to be capped by an artificial cap.

12. A dental implant according to claim 10, wherein each of said heads and each of said bodies are separate from each other, each said head having an externally threaded rod joined to a lower end thereof, each said body having an internally threaded boss in an upper central portion thereof, said head being detachably supported on said body with said externally threaded rod being threaded in said internally threaded boss.

* * * * *